US00PP29859P2

(12) United States Plant Patent
Page

(10) Patent No.: US PP29,859 P2
(45) Date of Patent: Nov. 20, 2018

(54) ***PHYSOSTEGIA* PLANT NAMED 'NICAUCA'**

(50) Latin Name: *Physostegia virginiana*
Varietal Denomination: Nicauca

(71) Applicant: Stephen Page, Oude Wetering (NL)

(72) Inventor: Stephen Page, Oude Wetering (NL)

( * ) Notice: Subject to any disclaimer, the term of this patent is extended or adjusted under 35 U.S.C. 154(b) by 0 days.

(21) Appl. No.: 15/731,493

(22) Filed: Jun. 19, 2017

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Physostegia* plant named 'Nicauca', characterized by its compact and upright plant habit; freely basal branching growth habit; long flowering period; purple-colored flowers arranged on dense terminal racemes; and good garden performance and winter hardiness.

2 Drawing Sheets

Botanical designation: *Physostegia virginiana.*
Cultivar denomination: 'NICAUCA'.

BACKGROUND OF THE INVENTION

The present invention relates to a new and distinct *Physostegia* plant, botanically known as *Physostegia virginiana*, commonly referred to as Obedience and hereinafter referred to by the name 'Nicauca'.

The new *Physostegia* plant is a product of a planned breeding program conducted by the Inventor in Hillegom, The Netherlands. The objective of the breeding program was to develop new compact *Physostegia* plants with good performance and attractive flower coloration.

The new *Physostegia* plant originated from an open-pollination during the summer of 2012 of *Physostegia virginiana* 'Vivid', not patented, as the female, or seed, parent with an unknown selection of *Physostegia virginiana* as the male, or pollen, parent. The new *Physostegia* plant was discovered and selected by the Inventor as a single flowering plant within the progeny of the stated open-pollination in an outdoor nursery in Hillegom, The Netherlands in October, 2013.

Asexual reproduction of the new *Physostegia* plant by divisions in a controlled environment in Hillegom, The Netherlands since March, 2014 has shown that the unique features of this new *Physostegia* plant are stable and reproduced true to type in successive generations.

SUMMARY OF THE INVENTION

Plants of the new *Physostegia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new

*Physostegia* plant. These characteristics in combination distinguish 'Nicauca' as a new and distinct *Physostegia* plant:

1. Compact and upright plant habit.
2. Freely basal branching growth habit.
3. Long flowering period.
4. Purple-colored flowers arranged on dense terminal racemes.
5. Good garden performance and winter hardiness.

Plants of the new *Physostegia* differ primarily from plants of the female parent, 'Vivid', in the following characteristics:

1. Plants of the new *Physostegia* are more compact and bushier than plants of 'Vivid'.
2. Plants of the new *Physostegia* flower for a longer period of time than plants of 'Vivid'.
3. Plants of the new *Physostegia* and 'Vivid' differ in flower color as plants of 'Vivid' have reddish pink-colored flowers.

Plants of the new *Physostegia* can be compared to plants of the *Physostegia virginiana* 'Pink Manners', disclosed in U.S. Plant Pat. No. 23,482. In side-by-side comparisons, plants of the new *Physostegia* differ primarily from plants of 'Pink Manners' in the following characteristics:

1. Plants of the new *Physostegia* are more compact than plants of 'Pink Manners'.
2. Plants of the new *Physostegia* start flowering later in the summer than plants of 'Pink Manners'.

BRIEF DESCRIPTION OF THE PHOTOGRAPHS

The accompanying photographs illustrate the overall appearance of the new *Physostegia* plant showing the colors as true as it is reasonably possible to obtain in colored reproductions of this type. Colors in the photographs may differ slightly from the color values cited in the detailed botanical description which accurately describe the colors of the new *Physostegia* plant.

The photograph on the first sheet is a side perspective view of a typical flowering plant of 'Nicauca' grown in a container.

The photograph on the second sheet is a close-up view of a typical flowering plant of 'Nicauca'.

DETAILED BOTANICAL DESCRIPTION

Plants used in the aforementioned photographs and following detailed description were grown in 19-cm containers during the summer and early autumn in an outdoor nursery in Hillegom, The Netherlands and under cultural practices typical of commercial *Physostegia* production. Plants were two years old when the photographs and description were taken. During the production of the plants, day temperatures ranged from 10° C. to 24° C. and night temperatures ranged from 3° C. to 14° C. In the following description, color references are made to The Royal Horticultural Society Colour Chart, 2015 Edition, except where general terms of ordinary dictionary significance are used.

Botanical classification: *Physostegia virginiana* 'Nicauca'.

Parentage:

*Female, or seed, parent.*—*Physostegia virginiana* 'Vivid', not patented.

*Male, or pollen, parent.*—Unknown selection of *Physostegia virginiana*, not patented.

Propagation:

*Type.*—By divisions.

*Time to initiate roots, summer.*—About eight to ten days at temperatures about 20° C.

*Time to initiate roots, winter.*—About 21 to 24 days at temperatures about 10° C.

*Time to produce a rooted young plant, summer.*—About eight weeks at temperatures about 15° C.

*Time to produce a rooted young plant, winter.*—About twelve weeks at temperatures about 12° C.

*Root description.*—Fine, fibrous; typically creamy white in color, actual color of the roots is dependent on substrate composition, water quality, fertilizer type and formulation.

*Rooting habit.*—Freely branching; dense.

Plant description:

*Plant and growth habit.*—Herbaceous perennial; compact and upright plant habit; roughly oblong in overall shape; moderately vigorous growth habit; moderate growth rate; flowers arranged on dense terminal racemes.

*Plant height, soil level to top of floral plane.*—About 44.5 cm.

*Plant width.*—About 34.8 cm.

*Lateral branch description.*—Quantity per plant: Freely basal branching habit with about nine primary branches each with about four lateral branches developing per plant during the flowering season. Length: About 26.8 cm. Diameter: About 6 mm. Internode length: About 1.6 cm. Strength: Strong. Aspect: Upright to about 20° from vertical. Texture and luster: Smooth, glabrous; moderately glossy. Color: Close to between 143B and 144A.

*Leaf description.*—Arrangement: Opposite, simple; sessile. Length: About 9.7 cm. Width: About 1.8 cm. Shape: Lanceolate to narrowly elliptic. Apex: Narrowly acuminate. Base: Truncate. Margin: Coarsely serrate. Texture and luster, upper surface: Smooth, glabrous, slightly leathery; slightly glossy. Texture and luster, lower surface: Smooth, glabrous, slightly leathery; matte. Venation pattern: Pinnate. Color: Developing leaves, upper surface: Close to 144B. Developing leaves, lower surface: Close to N144D. Fully expanded leaves, upper surface: Close to 137B; venation, close to 144A. Fully expanded leaves, lower surface: Close to 147B; venation, close to 144A to 144B.

Flower description:

*Flower type, arrangement and habit.*—Single tubular labiate flowers arranged on dense terminal racemes; freely flowering habit with about 80 flowers developing per inflorescence and about 2,500 flowers developing per plant during the flowering season; flowers with upper lip and three-lobed lower lip; flowers face mostly outwardly on the raceme.

*Natural flowering season.*—Relatively long flowering period; continuous from midsummer into the late autumn in The Netherlands.

*Flower longevity on the plant.*—Individual flowers last about ten days on the plant; flowers not persistent.

*Fragrance.*—None detected.

*Flower buds.*—Length: About 1 cm. Diameter: About 4 mm. Shape: Obovate, curved. Color: Close to 144B and 143B; distally, close to 77B.

*Inflorescence height.*—About 14.4 cm.

*Inflorescence diameter.*—About 4.6 cm.

*Flower diameter.*—About 1 cm.

*Flower depth (height).*—About 2.4 cm.

*Petals.*—Quantity and arrangement: Upper lip and lower lip, three-lobed; lower 67.5% of the petals are fused into a narrow tube. Length, upper lip: About 2.5 cm. Length, lower lip: About 2.5 cm. Width, upper lip: About 7 mm. Width, lower lip: About 1 mm. Shape, upper lip: Narrowly obovate. Shape, lower lip: Obovate. Apex, upper lip: Obtuse, rounded. Apex, lower lip: Three-lobed. Margin, upper and lower lips: Entire. Texture and luster, upper and lower lips, inner surface: Smooth, glabrous; slightly glossy. Texture and luster, upper and lower lips, outer surface: Densely pubescent; slightly glossy. Color: When opening, upper and lower lips, inner surface: Close to N78D; towards the base, close to N80D. When opening, upper lip, outer surface: Close to between N78B and NN78B; towards the base, close to N78C. When opening, lower lip, outer surface: Center lobe, close to 77D; lateral lobes, close to N78B to N78C. Fully opened, upper and lower lips, inner surface: Close to N78D; towards the base, close to N80D. Fully opened, upper lip, outer surface: Close to between N78B and NN78B; towards the base, close to N78C; color becoming closer to 83A with development. Fully opened, lower lip, outer surface: Center lobe, close to 77D; lateral lobes, close to N78B to N78C; color becoming closer to 83A with development.

*Sepals.*—Quantity and arrangement: Five, lower 75% fused into a campanulate calyx. Calyx length: About 8 mm. Calyx diameter: About 4 mm. Length: About 8 mm. Width: About 1.25 mm. Shape: Obovate. Apex: Acute. Margin: Entire. Texture and luster, inner and outer surfaces: Smooth, glabrous; matte. Color: When opening, inner surface: Close to 144C; distally, close to 143B. When opening, outer surface: Close to 144B; distally, close to 143B. Fully opened, inner surface: Close to 146C; distally, close to 147B. Fully opened, outer surface: Close to 146D; distally, close to 147B.

*Peduncles*.—Length: About 13.3 cm. Diameter: About 2.5 mm. Aspect: Mostly upright. Strength: Strong. Color: Close to 143B.

*Pedicels*.—Length: About 1 mm. Diameter: About 1 mm. Aspect: About 40° from peduncle axis. Strength: Strong. Color: Close to 143B.

*Reproductive organs*.—Stamens: Quantity per flower: Four. Filament length: About 2 cm. Filament color: Close to 77D. Anther shape: Broadly ovate, flattened. Anther length: About 1.25 mm. Anther color: Close to NN155B; margins, close to 202A. Pollen amount: Scarce. Pollen color: Close to 156D. Pistils: Quantity per flower: One. Pistil length: About 2.1 cm. Stigma shape: Cleft. Stigma color: Close to 77C. Style length: About 1.9 cm. Style color: Close to 77D. Ovary color: Close to 144C.

*Seeds and fruits*.—Seed and fruit production has not been observed on plants of the new *Physostegia* to date.

Disease & pest resistance: Plants of the new *Physostegia* have not been noted to be resistant to pathogens and pests common to *Physostegia* plants.

Garden performance: Plants of the new *Physostegia* have exhibited good garden performance and to tolerant rain, wind and to temperatures ranging from about −20° C. to about 40° C.

It is claimed:

1. A new and distinct *Physostegia* plant named 'Nicauca' as illustrated and described.

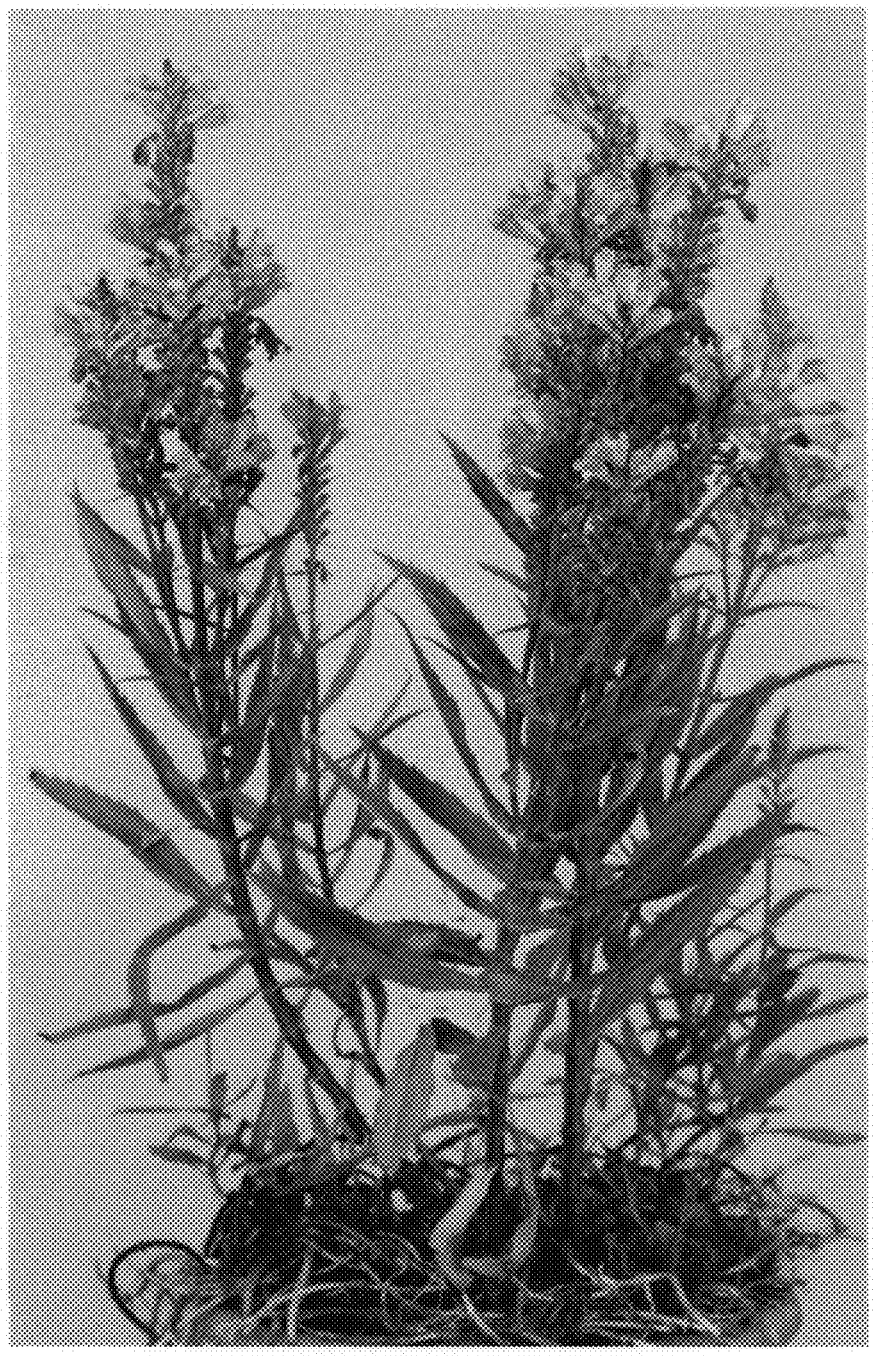

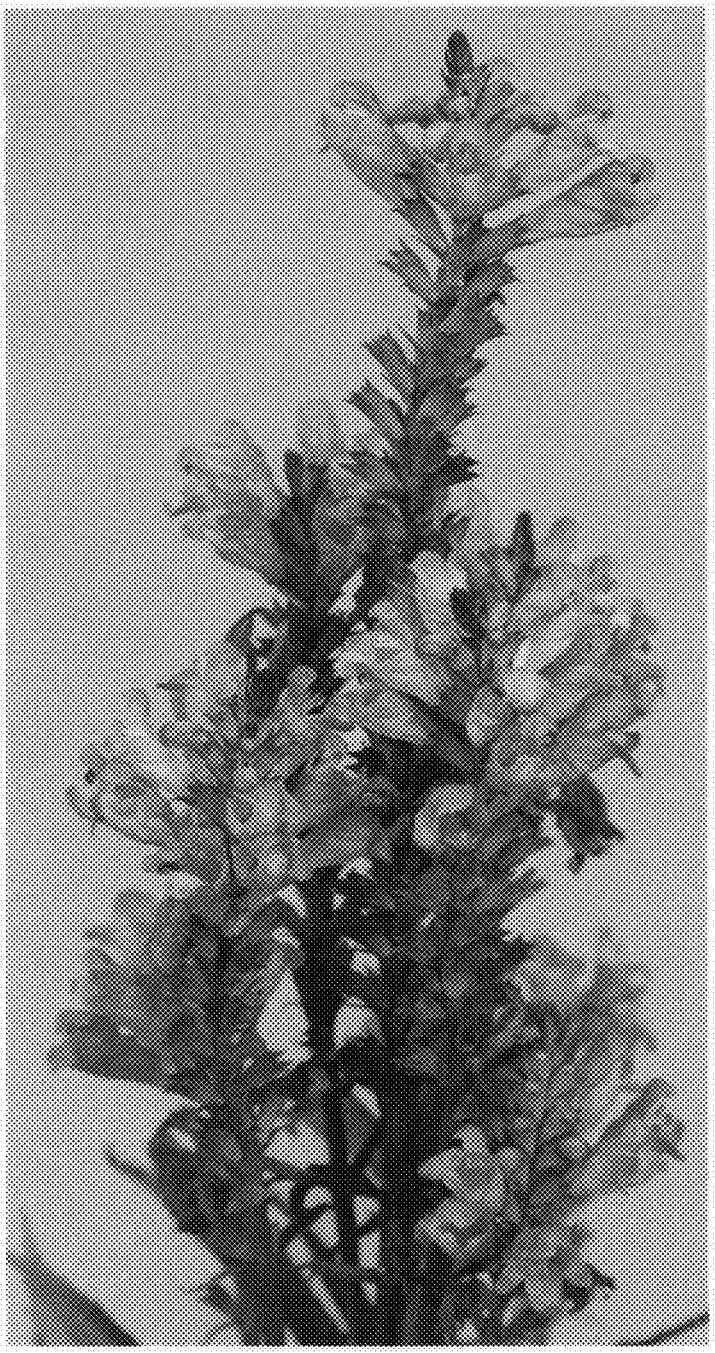

* * * * *